(12) United States Patent
Powell et al.

(10) Patent No.: US 7,683,221 B2
(45) Date of Patent: Mar. 23, 2010

(54) PROCESS FOR THE PRODUCTION OF ALKYLENE GLYCOLS USING HOMOGENEOUS CATALYSTS

(75) Inventors: Joseph Broun Powell, Houston, TX (US); Eugene Marie Godfried Andre Van Kruchten, Amsterdam (NL)

(73) Assignee: Shell Oil Company, Houston, TX (US)

( * ) Notice: Subject to any disclaimer, the term of this patent is extended or adjusted under 35 U.S.C. 154(b) by 389 days.

(21) Appl. No.: 10/862,172

(22) Filed: Jun. 4, 2004

(65) Prior Publication Data

US 2004/0267059 A1 Dec. 30, 2004

Related U.S. Application Data

(60) Provisional application No. 60/476,564, filed on Jun. 6, 2003.

(51) Int. Cl.
 *C07C 29/10* (2006.01)
(52) U.S. Cl. ..................... 568/867; 568/868
(58) Field of Classification Search .............. 568/867, 568/868
 See application file for complete search history.

(56) References Cited

U.S. PATENT DOCUMENTS

| | | | | |
|---|---|---|---|---|
| 1,982,688 A | * | 12/1934 | Pack | 423/182 |
| 4,160,116 A | | 7/1979 | Mieno et al. | 568/867 |
| 4,349,417 A | | 9/1982 | Rebsdat et al. | 203/33 |
| 4,524,224 A | | 6/1985 | Taylor et al. | 568/858 |
| 4,560,813 A | * | 12/1985 | Collier | 568/872 |
| 4,564,715 A | | 1/1986 | Briggs et al. | 568/867 |
| 4,760,200 A | | 7/1988 | Keen et al. | 568/867 |
| 4,822,926 A | | 4/1989 | Dye | 568/867 |
| 4,937,393 A | * | 6/1990 | Masuda et al. | 568/867 |
| 4,982,021 A | * | 1/1991 | Best et al. | 568/867 |
| 5,488,184 A | | 1/1996 | Reman et al. | 568/867 |
| 6,124,508 A | | 9/2000 | Van Kruchten | 568/867 |
| 6,137,014 A | * | 10/2000 | Godfried Andre Van Kruchten | 568/867 |
| 6,153,801 A | | 11/2000 | Van Kruchten | 568/867 |
| 7,105,710 B2 | | 9/2006 | Boons et al. | 568/867 |
| 2002/0082456 A1 | * | 6/2002 | Van Kruchten et al. | 568/867 |

FOREIGN PATENT DOCUMENTS

| | | |
|---|---|---|
| EP | 0160330 | 11/1985 |
| EP | 0226799 | 7/1987 |
| JP | 56118024 | 9/1981 |
| JP | 62116528 | 5/1987 |
| WO | WO 99/23053 | 5/1999 |
| WO | WO 00/35840 | 6/2000 |

\* cited by examiner

*Primary Examiner*—Rosalynd Keys

(57) ABSTRACT

A process for the manufacture of alkylene glycol by the hydration of alkylene oxide using a soluble catalyst that permits the separation of the reaction product into an alkylene glycol product stream and a recycle stream without the significant precipitation of the soluble catalyst from the recycle stream.

13 Claims, 1 Drawing Sheet

PROCESS FOR THE PRODUCTION OF ALKYLENE GLYCOLS USING HOMOGENEOUS CATALYSTS

This application claims the benefit of U.S. Provisional Application No. 60/476,564 filed Jun. 6, 2003, the entire disclosure of which is hereby incorporated by reference.

FIELD OF THE INVENTION

This invention relates to a process for the manufacture of alkylene glycol by reacting alkylene oxide with water in the presence of a homogeneous catalyst. Another aspect of the invention relates to a process for making alkylene glycol product by hydration of alkylene oxide in the presence of a soluble catalyst having solubility characteristics that permit the separation of the alkylene glycol product from the soluble catalyst.

BACKGROUND

Alkylene glycols, in particular monoalkylene glycols, are of established commercial interest. For example, monoalkylene glycols are being used in anti-freeze compositions, as solvents and as base materials in the production of polyalkylene terephthalates e.g. for fibers or bottles.

The production of alkylene glycols by liquid phase hydrolysis of alkylene oxide is known. The hydrolysis is performed without a catalyst by adding a large excess of water, e.g. 20 to 25 moles of water per mole of alkylene oxide, or with a smaller excess of water in a catalytic system. The reaction is considered to be a nucleophilic substitution reaction, whereby opening of the alkylene oxide ring occurs, water acting as the nucleophile. Because the primarily formed monoalkylene glycol also acts as a nucleophile, as a rule, a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product.

Considerable efforts have been made to find an alternative for increasing the reaction selectivity without having to use a large excess of water. Usually these efforts have focused on the selection of more active hydrolysis catalysts. The use of homogeneous catalysts can be particularly beneficial in the hydration of alkylene oxide if they can easily be separated from the reaction product. However, the use of catalysts in homogeneous reaction systems generally pose a problem when the reaction product is separated by distillation due to the low solubility of the catalyst compounds in the glycol product. The low solubility of the catalyst can result in the precipitation thereof during the separation of the reaction product.

An important step in the manufacture of alkylene glycol by the catalytic hydrolysis of alkylene oxide is the separation of the water, catalyst and reaction by-products from the alkylene glycol reaction product. It is thus necessary for the homogeneous catalyst used in such a process to have properties which permit the easy separation of the alkylene glycol from the other components of the reaction product.

Accordingly, there is a need to develop a process that uses an active but selective alkylene oxide hydration catalyst having solubility characteristics which permit easy separation of the alkylene glycol reaction product and other components of the reaction product for reuse in the hydration reaction.

Other aspects, objects, and the several advantages of the invention will become apparent in light of the following disclosure.

SUMMARY OF THE INVENTION

The invention is directed to a process for the manufacture of monoalkylene glycol. In this process, a reaction mixture, which comprises alkylene oxide, water and a soluble catalyst, is subjected to suitable reaction conditions for forming a reaction product comprising monoalkylene glycol, water, the soluble catalyst and, generally, reaction by-products such as higher alkylene glycols. The reaction product is separated into a monoalkylene glycol product stream, which comprises monoalkylene glycol, and a recycle stream comprising the soluble catalyst and the reaction by-product. The recycle stream is reused by combining it with the reaction mixture.

The invention is also directed to a process wherein a reaction mixture, which comprises alkylene oxide, water, and a soluble catalyst, is introduced into a reaction zone that is operated under suitable reaction conditions to thereby form a reaction product. The reaction product, which comprises monoalkylene glycol, water, the soluble catalyst and a reaction by-product, is withdrawn from the reaction zone and introduced into a separation system. The separation system provides for the separation of the reaction product into a monoalkylene glycol product stream and a recycle stream comprising the soluble catalyst and reaction by-product. The recycle stream is reused by adding it to the reaction mixture.

DETAILED DESCRIPTION

Figure 1:
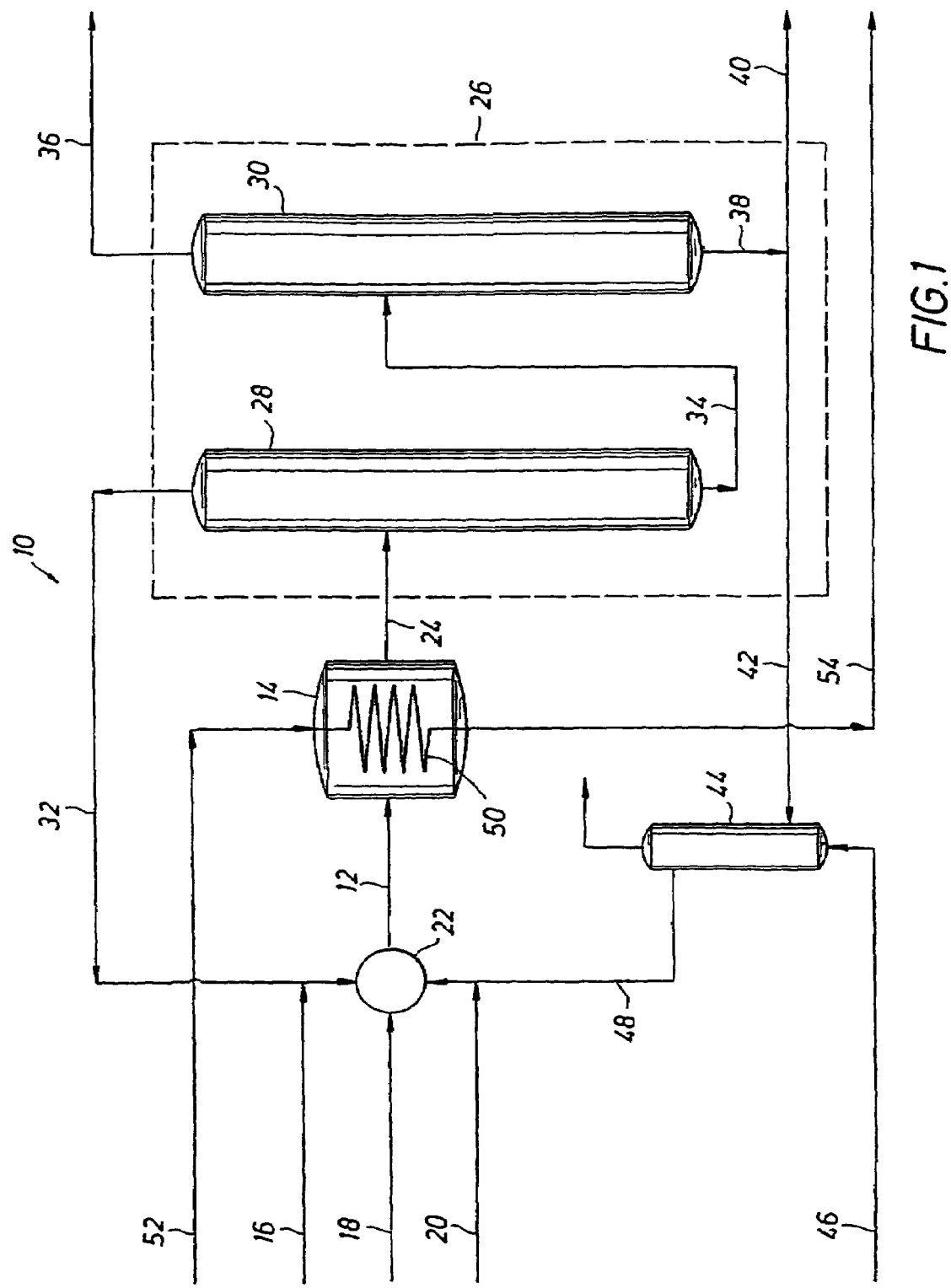
FIG. 1 is a schematic representation of one embodiment of the inventive process for the manufacture of monoalkylene glycol by hydrolysis of alkylene oxide using a soluble catalyst.

The inventive process includes the hydrolysis of alkylene oxide in a homogeneous liquid reaction system using a soluble catalyst compound having solubility properties that permit its separation from a reaction product without encountering the problems often associated with the use of other less soluble alkylene oxide hydrolysis catalyst compounds. Therefore, one important feature of the inventive process is in the use of an alkylene oxide hydrolysis catalyst compound that has good catalytic properties, such as providing for high alkylene oxide conversion and selectivity towards monoalkylene glycol, but which has the necessary solubility characteristics that allow the separation of the monoalkylene glycol reaction product from the hydrolysis catalyst. The separated hydrolysis catalyst can be reused in the hydrolysis of alkylene oxide.

The alkylene oxide hydrolysis catalyst of the invention is a high activity hydrolysis catalyst providing for a high reaction rate and conversion of the alkylene oxide reactant with good selectivity towards the monoalkylene glycol, therefore, providing for a minimum of yield in undesirable by-products such as the higher alkylene glycols such as dialkylene glycols, trialkylene glycols and polyalkylene glycols.

It is important to achieving the benefits of the invention for the alkylene oxide hydrolysis catalyst to have a high solubility in the hydrolysis reaction product and in the monoalkylene glycol reaction product mixture in order to minimize the precipitation of the alkylene oxide hydrolysis catalyst during the separation of the reaction product. Thus, the solubility of the alkylene oxide hydrolysis catalyst in monoalkylene glycol can generally exceed 5 weight percent. The preferred solubility of the soluble catalyst in monoalkylene glycol exceeds 6 weight percent and, most preferred, the solubility exceeds 8 weight percent.

When referring to the solubility of the alkylene oxide hydrolysis catalyst, or soluble catalyst, the term weight percent means the ratio of the total weight of the soluble catalyst that can be dissolved in a given weight of a specified alkylene glycol, such as ethylene glycol, including monoethylene glycol and diethylene glycol, at a temperature of 25° C., to form a saturated solution divided by the given weight of the specified alkylene glycol.

Any bicarbonate salt, carboxylate salt or metalate salt, for example, a molybdate salt, having the solubility characteristics described above and that is effective as an alkylene oxide hydrolysis catalyst can be used in the inventive process. Possible bicarbonate salts include sodium bicarbonate, potassium bicarbonate, phosphonium bicarbonate, choline bicarbonate and ammonium bicarbonate; but, among these, the preferred bicarbonate salts are potassium bicarbonate, phosphonium bicarbonate and ammonium bicarbonate. The most preferred bicarbonate salt is potassium bicarbonate. Possible carboxylate salts include potassium formate, barium formate, and lead formate. Potassium molybdate is one possible molybdate salt that may be used as a catalyst.

It is preferred for the alkylene oxide hydrolysis reaction to proceed as a homogeneous liquid phase reaction within a reaction zone under suitable hydrolysis reaction conditions. Thus, a reaction mixture can be introduced into a reaction zone within which the reaction mixture is subjected to suitable reaction conditions to form a reaction product containing the alkylene glycol, preferably monoalkylene glycol, that corresponds to the alkylene oxide of the reaction mixture.

The reaction mixture that is introduced into the reaction zone comprises the alkylene oxide reactant, water and the soluble catalyst in the proportions that are effective in producing the resulting monoalkylene glycol reaction product. Generally, it is desirable to use as close to the stoichiometric amount of water, based on the alkylene oxide, as is practical considering the selectivity to monoalkylene glycol that is obtainable from the particular soluble catalyst compound used. But, generally, the amount of water used in the reaction mixture can exceed the stoichiometric requirements such that the amount of water in the reaction mixture is in the range of from 1 to 15 moles of water per mole of alkylene oxide. It is preferred for the amount of water present in the reaction mixture to be in the range of from 1 to 6 moles of water per mole of alkylene oxide.

As for the soluble catalyst concentration in the reaction mixture, it is generally desirable for the concentration of soluble catalyst in the reaction mixture to be an effective concentration to catalyze the alkylene oxide hydrolysis reaction and to preferably provide a high conversion of the alkylene oxide with a high selectivity to the corresponding monoalkylene glycol. What is meant by high conversion of alkylene oxide is the reaction thereof as determined by the amount of alkylene oxide in the reaction mixture that is not present in the reaction product withdrawn from the reaction zone. Percent conversion is determined by the ratio of the amount of alkylene oxide reacted divided by the amount of alkylene oxide originally present in the reaction mixture, multiplied by 100. The alkylene oxide conversion generally is greater than 90 percent, but preferably greater than 95 percent and, most preferably, greater than 98 percent.

As noted, it is also preferred for the soluble catalyst to provide for a high selectivity of the converted alkylene oxide to its corresponding monoalkylene glycol. Generally, the selectivity exceeds 90 percent, but preferably, the selectivity exceeds 95 percent and, most preferably, 98 percent. Percent selectivity as used herein is defined as the ratio of the total moles of converted alkylene oxide converted to its corresponding monoalkylene glycol divided by the total moles of alkylene oxide converted, the ratio being multiplied by 100. Due to the high selectivity provided by the soluble catalyst of the inventive process, the quantity of reaction by-products, such as the higher alkylene glycols, resulting from the secondary reaction between monoalkylene glycol and alkylene oxide is minimized. The secondary reaction is a competing reaction to the alkylene oxide hydrolysis reaction.

The soluble catalyst concentration in the reaction mixture is such that it provides the aforedescribed benefits and can range up to its solubility limits in the reaction mixture and process recycle streams. The soluble catalyst concentration, however, is best in the range of from 0.01 weight percent to 10 weight percent based on the total weight of the reaction mixture. Preferably, the catalyst concentration in the reaction mixture is in the range of from 0.1 weight percent to 8 weight percent, and, most preferably, from 1 weight percent to 6 weight percent.

The alkylene oxides used in the reaction mixtures of the process of the invention have their conventional definition, i.e., they are compounds having a vicinal oxide (epoxy) group in their molecules.

Particularly suitable are alkylene oxides of the general formula

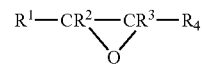

wherein $R^1$ to $R^4$ independently represent a hydrogen atom or an, optionally substituted, alkyl group having from 1 to 6 carbon atoms. Any alkyl group, represented by $R^1$, $R^2$, $R^3$, and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$-$C_3$-alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane, 2,3-epoxybutane and glycidol. Ethylene oxide and propylene oxide are of particular commercial importance. The preferred alkylene oxide is ethylene oxide.

The reaction step of the invention can be carried out in a continuous or a batch operation. However, for large scale embodiments it is preferred to operate the reaction zone of the process continuously.

The reaction zone can be maintained under isothermal, adiabatic or hybrid conditions. Any suitable reactor means known to those skilled in the art can be used to define the reaction zone and to provide the desired isothermal, adiabatic or hybrid reaction zone conditions. To achieve isothermal reaction zone conditions, it is preferred to use an isothermal reactor means generally of the shell-and-tube reactor type. A shell-and-tube reactor typically includes multiple tubes contained within a shell. It is preferred for the reaction mixture to pass through the tube side of the shell-and-tube reactor and for the coolant to pass through the shell side of the shell-and-tube reactor. To achieve adiabatic reaction zone conditions, no substantial cooling of the hydrolysis reaction occurs. Preferably, the reaction product from the adiabatic reactor means passes to a separate heat exchanger which defines a heat transfer zone and provides means for removing heat energy from the reaction product. In certain circumstances, it can be advantageous to use a recycle reactor by which at least a portion of the reaction product is recycled and returned as a feed to the recycle reactor.

The reaction conditions maintained within the reaction zone of the inventive process are such that there is a high conversion of alkylene oxide hydrated to its corresponding monoalkylene glycol. The reaction temperature is generally in the range of from 50° C. to 200° C., preferably, from 80° C. to 160° C. and, most preferably, from 90° C. to 150° C. The reaction pressure is generally in the range of from 100 kPa to 10,000 kPa, preferably from 150 kPa to 2500 kPa and, most preferably, from 200 kPa to 2000 kPa.

One advantage of the inventive process is the yield of a reaction product having a low concentration of reaction by-products such as dialkylene glycols, trialkylene glycols and polyalkylene glycols. This is partly due to the performance of the soluble catalysts of the invention providing for a high selectivity to monoalkylene glycol. When the alkylene oxide of the reaction mixture is ethylene oxide, typical reaction by-products include diethylene glycol and triethylene glycol.

The amount of reaction by-products formed in the reaction zone can run upwardly to 10 weight percent, based on the monoalkylene glycol of the reaction product, or even higher depending upon the molar ratio of water to alkylene oxide in the reaction mixture. It is preferred for the amount of reaction by-product formed in the reaction zone to be as low as possible and, thus, less than 5 weight percent, preferably, less than 3 weight percent and, most preferably, less than 1 weight percent based upon monoalkylene glycol of the reaction product.

Due to the use of the high activity soluble catalyst and favorable reaction conditions such as reaction temperature and residence time, substantially all the alkylene oxide in the reaction mixture is converted thus providing a reaction product generally having a low concentration of unreacted alkylene oxide. The reaction product can have a concentration of alkylene oxide of less than 3 weight percent of the total weight of the reaction product and, more typically, the concentration of alkylene oxide is less than 2 weight percent.

Because an excess amount of water is generally used in the hydrolysis reaction, the amount of water in the reaction product can be in the range of from 10 to 90 weight percent, but more typically from 20 to 80 weight percent and, most typically from 30 to 70 weight percent. The alkylene glycol concentration in the reaction product can be in the range of from 10 to 90 weight percent, more typically, from 20 to 80 weight percent and, most typically, from 30 to 70 weight percent.

To separate the monoalkylene glycol from the reaction product to give an monoalkylene glycol product stream, the reaction product is preferably introduced into a separation system that provides means for separating the reaction product into a monoalkylene glycol product stream that comprises monoalkylene glycol and a first recycle stream that comprises at least a portion, and can include substantially all, of the soluble catalyst of the reaction product and at least a portion of the reaction by-products of the reaction product.

It is a preferred aspect of the invention for the separation system to further provide for the separation of the reaction product into a second recycle stream that comprises water. The soluble catalyst of the first recycle stream and the water of the second recycle stream can be reused in the hydrolysis reaction by combining them with the reaction mixture being fed to the reaction zone of the process system.

The monoalkylene glycol product stream is generally a high purity stream with the concentration of monoalkylene glycol being at least 90 weight percent of the total weight of the monoalkylene glycol product stream. Preferably, however, the concentration of monoalkylene glycol is at least 95 weight percent of the monoalkylene glycol product stream and, most preferably, the concentration is at least 98 weight percent.

It is desirable to recover as much of the monoalkylene glycol from the reaction product as is permitted by the overall manufacturing process, but, generally, at least 40 or even at least 50 weight percent of the monoalkylene glycol of the reaction product can be recovered per pass through the reaction and separation steps of the overall monoalkylene glycol manufacturing process to thereby provide the monoalkylene glycol product stream. The monoalkylene glycol not recovered per pass can be recycled to the reaction zone with either the first recycle stream, or the second recycle stream, or both. Thus, a major portion of the monoalkylene glycol of the reaction product is ultimately recovered with the monoalkylene glycol product stream generally exceeding 95 weight percent, or even exceeding 98 weight percent of the monoalkylene glycol yielded from the reaction zone.

The first recycle stream includes most of the reaction by-products and monoalkylene glycol not recovered with the monoalkylene glycol product stream. The first recycle stream can have a concentration of monoalkylene glycol in the range of from 0 or upwardly to 90 weight percent and a concentration of reaction by-products in the range of from 10 to 100 weight percent of the total weight of the first recycle stream.

A problem that is encountered with the use of many homogeneous catalyst systems in the manufacture of monoalkylene glycols is the precipitation of the catalyst during the separation of the monoalkylene glycol product from the other components of the reaction product. By using the particular soluble catalyst as described herein, the problems associated with catalyst precipitation during the separation of the reaction product are minimized.

In the operation of the inventive process, the amount of mono and higher alkylene glycols that is recycled to the reaction zone may be optimized relative to the soluble catalyst concentration in the reaction zone feed and the solubility limits of the soluble catalyst in the first recycle stream. The soluble catalyst will typically be more soluble in the reaction zone feed than in the first recycle stream due to the relatively larger amount of water present therein. By increasing the relative amount of alkylene glycol (due to the removal of water and monoalkylene glycol) recycled to the reaction zone, the concentration of soluble catalyst in the recycle stream is reduced thereby minimizing the potential for soluble catalyst precipitation during distillation and recycle. However, with the increased recycle of alkylene glycol the reaction selectivity decreases via the formation of higher alkylene glycols. The use of higher soluble catalyst concentrations in the reaction zone feed can improve the reaction selectivity, but it may require use of a soluble catalyst of greater solubility, or an increase in the recycle of alkylene glycol via the first recycle stream, to avoid precipitation.

While the water, soluble catalyst and reaction by-products are separated from the reaction product and can be reused by combining them with the reaction mixture, the separation step can cause some of the soluble catalyst to decompose. In the case where the soluble catalyst is a bicarbonate salt, the high temperatures associated with the distillation separation of the reaction product can cause the decomposition of a portion of the bicarbonate salt to carbonate compounds. It can, thus, be beneficial to convert the carbonates that are contained in the first recycle stream to bicarbonate by the use of a carbon dioxide contacting step whereby the first recycle stream is contacted with carbon dioxide under suitable contacting and conversion conditions. Typical means for contacting the first recycle stream with a gas phase reactant ($CO_2$) can include, for example, gas-sparged bubble columns, stirred tanks loop reactors designed for gas dispersion, equipment used for gas absorption including packed or trayed towers with counter-flow feed of liquid, venturi scrubbers or liquid spray scrubbers.

An alternative to the use of the carbon dioxide contacting step is to reduce or even eliminate the decomposition of the bicarbonate salts that occurs in the separation step. The decomposition of the bicarbonate salt can be reduced by the use of separation means such as a wiped-film evaporator, a falling film evaporator or other separation means that define a separation zone and provide means for the short contact time and for lower temperature separation than alternative distillation methods so as to minimize or avoid the thermal degradation of the bicarbonate salt.

As a result of the recycling of the reaction by-products contained in first recycle stream there can be a buildup in the first recycle stream to undesirable levels. It is thus necessary to remove a portion of the recycle stream, preferably by use of a purge stream, from the process system in order to keep the concentration of the reaction by-products in the first recycle stream at acceptable levels.

Now referring to FIG. 1, presented is a simplified schematic representation of process system 10, which exemplifies a process for manufacturing monoalkylene glycol in which soluble catalyst is recycled to the reaction zone following distillation to recover monoalkylene glycol product, in accordance with the invention. A reaction mixture comprising alkylene oxide, water, and a soluble catalyst is formed for introduction by way of conduit 12 into reactor 14. Reactor 14 defines a reaction zone, operated under suitable reaction conditions, and provides means for reacting the alkylene oxide and water of the reaction mixture to thereby form monoalkylene glycol. The reaction mixture can be prepared prior to its introduction into reactor 14 by introducing alkylene oxide through conduit 16, water through conduit 18 and makeup catalyst through conduit 20 to mixer 22. Mixer 22 defines a mixing zone, operated under suitable mixing conditions, and provides means for mixing the components of the reaction mixture.

Reactor 14 is appropriately designed and sized so as to provide the necessary contacting and residence time conditions to provide a reaction product as described herein. The reaction product is withdrawn from reactor 14 through conduit 24 as a reactor effluent which is passed to separation system 26. Separation system 26 defines a separation zone and provides means for separating the reaction product into multiple streams which include a monoalkylene glycol product stream, a first recycle stream and second recycle stream.

It is preferred for separation system 26 to include distillation unit 28 and vacuum distillation unit 30. The reaction product passing through conduit 24 is fed to distillation unit 28. Distillation unit 28 defines a distillation separation zone and provides means for separating water and other possible volatile byproducts or components from the reaction product. The separated water passes from distillation unit 28 through conduit 32 as second recycle stream comprising water. A portion of the water and volatile byproducts or components (if present) may be purged, or subjected to further separation steps, to a second recycle stream that is substantially free of volatile, nonreactive components. The distillation unit 28 bottoms product, which comprises monoalkylene glycol, soluble catalyst and reaction by-products, passes from distillation unit 28 through conduit 34 and is fed to vacuum distillation unit 30. Vacuum distillation unit 30 defines a vacuum distillation separation zone and provides means for separating the monoalkylene glycol of the bottoms product from the soluble catalyst and reaction by-products. The separated monoalkylene glycol passes as a product stream from vacuum distillation unit 30 by way of conduit 36. The bottoms of vacuum distillation unit 30 preferably comprises recovered soluble catalyst and reaction by-products but can also comprise monoalkylene glycol or water, or both. It further can contain decomposed soluble catalyst. The bottoms of vacuum distillation unit 30 pass from vacuum distillation unit 30 through conduit 38 as a first recycle stream.

Process system 10 can be purged of buildup of reaction by-product by use of a purge stream. A portion of first recycle stream passing through conduit 38 can be removed as a purge stream through conduit 40 with the remaining portion of the first recycle stream passing by way of conduit 42 to contactor 44. Contactor 44 defines a contacting zone and provides means for contacting carbon dioxide with the first recycle stream to thereby convert at least a portion of the decomposed soluble catalyst in the first recycle stream back to its original undecomposed form. Carbon dioxide gas is introduced into contactor 44 through conduit 46 and the carbon dioxide treated, first recycle stream passes from contactor 44 through conduit 48 to mixer 22 whereby the first recycle stream is added to the reaction mixture for reuse. Additionally, the second recycle stream, comprising water, passes through conduit 32 to mixer 22 to be added to the reaction mixture for reuse.

The hydrolysis reaction is typically an exothermic reaction. To control the temperature of the reaction zone defined by reactor 14 a coolant may be used to remove heat, by indirect heat exchange, from the reaction zone. The coolant is passed to cooling coils 50 of reactor 14 through conduit 52 and is removed therefrom through conduit 54. As an alternative, control of the temperature of the reaction zone may be accomplished by the cooling of the reaction zone feeds prior to their introduction into reactor 14.

The following examples are intended to illustrate certain of the advantages of the present invention and are not intended to unduly limit the scope of the invention.

Example I

This Example I describes the experimental procedure used to determine the reaction kinetics and selectivities of an ethylene oxide hydrolysis reaction system for a thermal reaction, a resin catalyzed reaction, and two soluble catalyst system catalyzed reactions. This Example I also presents comparative data showing the benefits from using a soluble catalyst system versus the use of either a resin catalyst or no catalyst, i.e., thermal reaction.

Batch experiments were conducted using a 100-ml stainless steel screw cap autoclave ("miniclave") fitted with pressure relief valves and heated via an oil bath. The contents of the miniclave reactor were mixed using a Teflon stir bar.

For the catalyzed reactions, the miniclave reactor was first charged with catalyst and purged with nitrogen, and then filled with nominally from 50-70 ml of a mixture of ethylene oxide (EO) in water/ethylene glycol (EG). Dosing of EO into the water/EG mixtures was accomplished safely under nitrogen pressure using a sight glass delivery system. The charged miniclave reactor was then topped with nitrogen pressure to 5000 kPa for safe handling of EO, and placed in the oil bath for heat up and initiation of reaction. Use of a small bore 1/16-inch dip tube allowed sampling at different times during the reactions for gas chromatograph analysis to assess reaction kinetics. For the thermal reaction, the same aforedescribed procedure was used with the exception that no catalyst was charged to the miniclave reactor.

Table 1 presents the results from performing five different ethylene oxide hydrolysis reactions, including: (1) a thermal reaction; (2) a resin catalyzed reaction using an ion exchange resin catalyst in the bicarbonate form (Amberjet 4200/bicarbonate); (3) a potassium bicarbonate catalyzed reaction at a lower catalyst concentration; (4) a potassium bicarbonate catalyzed reaction at a higher catalyst concentration; and (5) a sodium bicarbonate catalyzed reaction. The data show the weight percent of ethylene oxide, ethylene glycol and diethylene glycol (undesired by-product) in the reaction mixture at the beginning of the reaction runs and at various other times during the reaction runs, as determined by gas chromatographic analysis.

Also presented are the ethylene oxide conversion, the molar selectivity to the desired monoethylene glycol (MEG) reaction product, the overall first-order reaction rate constant for the reaction mixture, and a "catalytic" rate constant calculated as the first-order rate above that expected from thermal reaction, normalized by the concentration of catalyst present. Under these conditions, diethylene glycol was the major byproduct formed.

The data demonstrate that all the catalyzed reactions exhibited better rates of ethylene oxide conversion, and better selectivity at a given conversion of ethylene oxide, than the thermal reaction. The soluble catalysts exhibited a performance comparable to the resin catalyst, relative to the catalyst concentrations employed. It is noted that the soluble catalyst at a high concentration provides a five-fold or more selectivity improvement as compared to the thermal reaction. The soluble potassium bicarbonate catalyzed reaction provides comparable performance as compared to the sodium bicarbonate catalyzed reaction, in both rate and selectivity.

TABLE 1

| Reaction | Sample No. | Catalyst | Catalyst eq/L | Time Hours | EO wt % | EG wt % | DEG wt % | EO Conversion (%) | MEG Selectivity | Overall rate 1/hr | Catalyst rate: 1/h/(eq/L) |
|---|---|---|---|---|---|---|---|---|---|---|---|
| A. Thermal Reaction | 1 | thermal | 0.00 | 0 | 10.152 | 19.200 | 0.029 | 0.00 | na | 0.44 | na |
| | 2 | thermal | 0.00 | 2.5 | 5.197 | 26.182 | 0.069 | 48.8 | 98.8% | | |
| | 3 | thermal | 0.00 | 4 | 1.648 | 31.183 | 0.528 | 83.8 | 94.8% | | |
| | 4 | thermal | 0.00 | 5 | 0.526 | 32.764 | 1.142 | 94.8 | 90.2% | | |
| B. Resin Catalyzed Reaction | 1 | IER-4200BC | 0.10 | 0 | 10.245 | 21.445 | 0.069 | 0.00 | na | 0.80 | 3.51 |
| | 2 | IER-4200BC | 0.10 | 1 | 5.143 | 28.634 | 0.078 | 49.8 | 98.7% | | |
| | 3 | IER-4200BC | 0.10 | 2.5 | 2.435 | 32.449 | 0.354 | 76.2 | 96.2% | | |
| | 4 | IER-4200BC | 0.10 | 5 | 0.035 | 35.832 | 0.495 | 99.7 | 96.0% | | |
| C. Potassium Bicarbonate Catalyzed Reaction | 1 | K-Bicarb | 0.33 | 0 | 18.789 | 15.000 | 0.000 | 0.00 | na | 1.54 | 3.30 |
| | 2 | K-Bicarb | 0.33 | 1 | 3.907 | 35.970 | 0.560 | 79.2 | 96.9% | | |
| | 3 | K-Bicarb | 0.33 | 2.5 | 0.442 | 40.853 | 1.190 | 97.6 | 94.6% | | |
| D. Potassium Bicarbonate Catalyzed Reaction | 1 | K-Bicarb | 0.51 | 0 | 15.690 | 15.000 | 0.000 | 0.00 | na | 1.49 | 2.07 |
| | 2 | K-Bicarb | 0.51 | 1 | 5.400 | 29.500 | 0.033 | 65.6 | 99.7% | | |
| | 3 | K-Bicarb | 0.51 | 2.5 | 00.248 | 36.759 | 0.218 | 98.4 | 98.8% | | |
| E. Sodium Bicarbonate Catalyzed Reaction | 1 | Na-Bicarb | 0.56 | 0 | 14.245 | 15.000 | 0.000 | 0.00 | na | 1.56 | 2.01 |
| | 2 | Na-Bicarb | 0.56 | 1 | 3.755 | 29.781 | 0.031 | 73.6 | 99.8% | | |
| | 3 | Na-Bicarb | 0.56 | 2.5 | 0.442 | 34.450 | 0.213 | 96.9 | 98.7% | | |

Example II

This Example II is presented to compare the solubilities of potassium bicarbonate and sodium bicarbonate in a liquid material resulting from the substantial removal of water and monoethylene glycol from an ethylene oxide hydrolysis reaction product. The liquid material is representative of the bottoms fraction of a distillation system for separating an ethylene oxide hydrolysis reaction effluent into an ethylene glycol product and a bottoms recycle product.

Aqueous products from sodium bicarbonate (Sample E) and potassium bicarbonate (Sample D) batch kinetics runs were distilled in a Bantam-ware short path still, to remove water and recover that portion of the monoethylene glycol (MEG) made in reaction. The objective was to determine whether it would be possible to recover ½ of the final MEG as product (the amount made in forward reaction), and recycle the remaining MEG with catalyst as a soluble phase. Water removal was accomplished at atmospheric pressure, while vacuum was applied (200 mm Hg absolute pressure or 0.26 atmospheres) for MEG removal at a bottoms temperature of 140-160° C.

Table 2 presents the results from performing the product distillation. Prolific precipitation of the sodium bicarbonate catalyst was observed when Sample E was distilled; however, on the other hand, the potassium bicarbonate catalyst system remained soluble in the final bottoms residue.

TABLE 2

| | | Sample D | Sample E |
|---|---|---|---|
| Bicarbonate cation | | K | Na |
| Catalyst initial | wt % | 4.33 | 3.50 |
| Initial Charge | grams | 68.25 | 65.28 |
| Water Removed | grams | 45.02 | 44.07 |
| MEG in distillate | grams | 10.20 | 12.00 |
| MEG bottoms | grams | 13.03 | 9.21 |
| Catalyst in bottoms (1-phase or slurry) | wt % | 22.67 | 24.79 |

TABLE 2-continued

|  |  | Sample D | Sample E |
|---|---|---|---|
| Catalyst precipitate in bottoms | yes/no | no (soluble/ 1-phase) | yes (solid slurry) |

These results show that the MEG can be recovered from an ethylene oxide hydrolysis reaction effluent with the potassium carbonate catalyst being soluble in the remaining reactor product thereby permitting its recycle with no precipitation of the potassium bicarbonate.

Example III

This Example III provides further comparisons of the solubilities of potassium bicarbonate and sodium bicarbonate.

The solubility studies were conducted via use of vials in a block heater. The results of the studies of the potassium bicarbonate and sodium bicarbonate solubilities in monoethylene glycol are presented in Table 3. The potassium bicarbonate and carbonate were found to be quite soluble in pure MEG (in excess of 15 weight percent), as is required for the distillation recycle process. Sodium bicarbonate was observed to be substantially less soluble than potassium bicarbonate.

TABLE 3

| Experiments | T (C.) | Anion | Cation | MEG wt % | Bicarb salt wt % | Solubility |
|---|---|---|---|---|---|---|
| 1 | 80 | K | bicarb | 30.02 | 14.91 | soluble |
| 2 | 80 | K | bicarb | 35.32 | 17.54 | soluble |
| 3 | 80 | K | bicarb | 50.00 | 50.00 | precipitate |
| 4 | 100 | K | bicarb | 83.33 | 16.67 | soluble |
| 5 | 100 | Na | bicarb | 86.21 | 13.79 | precipitate |
| 6 | 100 | K | carb | 82.43 | 17.57 | sol. limit |
| 7 | 100 | Na | carb | 98.49 | 1.51 | sol. limit |

Experiments 6 and 7 involved heating either excess potassium carbonate or excess sodium carbonate in MEG overnight with stirring, followed by titration of supernatant to observe the amount of soluble salt. The solubility of K-carbonate was 10-fold greater than the solubility of Na-carbonate. Since a portion of bicarbonate may decompose to carbonate under distillation recycle conditions, solubility of the carbonate salts is important to the effective operation of an ethylene oxide hydrolysis process that uses a homogeneous catalyst system. Current results indicate a recycle concentration of 17 wt % of the K-form salt in MEG distillation bottoms may safely be used for process design, regardless of carbonate or bicarbonate as anion.

Example IV

This Example IV describes the experimental procedure used to measure the solubilities of sodium, potassium and ammonium bicarbonate salts in the alkylene glycols of either monoethylene glycol (MEG) or diethylene glycol (DEG). Presented in this Example IV are the measured solubilities of the aforementioned bicarbonate salts in the relevant alkylene glycol.

The solubility of the particular bicarbonate salt was measured by first filling a vial with 7 grams of an alkylene glycol (either monoethylene glycol or diethylene glycol) and 3 grams of a bicarbonate salt (either sodium bicarbonate, potassium bicarbonate, or ammonium bicarbonate) and rotating for 18 hours. After rotating, supernatant samples were withdrawn, filtered via a 0.5 micron syringe filter, and titrated for soluble bicarbonate content. Table 4 presents the results of these solubility measurements.

TABLE 4

| | 25° C. Solubility of Bicarbonate Salts in Either MEG or DEG | | |
|---|---|---|---|
| Cation | Solvent | Solubility Equiv/Liter | Solubility wt % HCO$_3$ |
| Na | MEG | 0.79 | 4.83 |
| K | MEG | 1.41 | 8.57 |
| NH$_4$ | MEG | 2.08 | 12.66 |
| Na | DEG | 0.34 | 2.05 |
| K | DEG | 0.80 | 4.85 |
| NH$_4$ | DEG | 1.09 | 6.63 |

As may be observed from the data presented in Table 4, ammonium bicarbonate has a greater solubility in both MEG and DEG than does potassium bicarbonate, and potassium bicarbonate has a greater solubility in both MEG and DEG than does sodium bicarbonate. It is also noted that the bicarbonates are more soluble in MEG than in DEG. Diethylene glycol is a typical byproduct of an ethylene oxide hydration reaction and can be expected to be a substantial component of a soluble catalyst recycle stream in an alkylene glycol manufacturing process. It is noted that the solubilities of the potassium bicarbonate and ammonium bicarbonate in DEG exceeded 4 weight percent which make them particularly good soluble catalysts for alkylene oxide hydration. It is also noted that the solubilities of the potassium bicarbonate and ammonium bicarbonate in MEG exceeded 5 weight percent and even 8 weight percent.

Example V

This Example V demonstrates soluble catalyst recycle and the use of carbon dioxide to reformulate bicarbonate catalyst that is degraded to carbonate form during the distillation recovery of alkylene oxide product.

A 500-ml stirred batch reactor was charged with a mixture of 15 wt % MEG in water containing 7.1 wt % potassium bicarbonate soluble catalyst. The mixture was heated under N$_2$ atmosphere (7000 kPa) to 80° C., before the addition of 18 grams of ethylene oxide. Conversion was 99.1% after 4 hours, corresponding to a rate constant (adjusted to 90° C.) of 2.7 l/h/(eq/L) for the catalyzed reaction, relative to the thermal reaction.

The mixture was distilled in a batch still to remove water and a portion of the MEG product, with a maximum bottoms temperature of 136° C., over a period of 6.5 hours. No precipitates were observed in the bottoms produced while heated at distillation temperature. A final bottoms fraction containing MEG and trade DEG (diethylene glycol) yielded 36.6 grams.

Titration of the bottoms fraction indicated 91% retention of potassium carbonate or bicarbonate catalyst. Small loss of catalyst can be attributed to sampling for analysis. 93% of the bicarbonate had degraded to carbonate via loss of carbon dioxide during distillation.

The bottoms mixture containing degraded catalyst was blended with an amount of water required for a second reaction cycle, and sparged with carbon dioxide for one hour at ambient temperature (22° C.). Titration revealed virtually complete regeneration of bicarbonate, with 97.5% in bicarbonate form vs. 2.5% carbonate.

244 grams of the water-diluted recycle mixture were recycled to the reactor for a second reaction, conducted at 90° C., and also entailing addition of 18 grams of ethylene oxide. A conversion of 99.3% was obtained in only 3 hours, for a calculated catalytic rate constant of 3.0 l/h/(eq/L). Titration of the reaction mixture indicated 96.0% of the catalyst remaining in bicarbonate form, indicating negligible catalyst degradation during reaction. Reaction selectivity to MEG was 96%, indicating successful recycle and regeneration of selective bicarbonate catalyst.

Rate constants for the recycle demonstration experiment compare favorably with the smaller-scale results reported in Table 1 of above Example I.

Example VI

This Example VI is presented to compare the solubilities of potassium bicarbonate and sodium bicarbonate in either monoethylene glycol (MEG) or diethylene glycol (DEG) at a high temperature condition and the relative amounts of decomposition of the bicarbonate at such temperature condition.

The solubilities of bicarbonate salts of sodium and potassium were examined at 90° C. by heating excess solid with either MEG or DEG in a block heater, with periodic shaking, followed by titration of a sample of supernatant with 0.1 N HCl.

Table 5 presents the results of the solubility measurements and the measurement of decomposition of the bicarbonate to carbonate.

TABLE 5

Bicarbonate Solubility at 90° C.

| Cation | Solvent | Solubility equiv/Liter | Solubility $HCO_3$ wt % | % decomp* |
|---|---|---|---|---|
| Na | MEG | 1.28 | 7.82 | 1.9% |
| K | MEG | 2.39 | 14.57 | 9.7% |
| Na | DEG | 0.38 | 2.33 | 2.3% |
| K | DEG | 1.22 | 7.47 | 14.7% |

*to carbonate

The results presented in Table 5 for bicarbonate salts show enhanced solubility for potassium bicarbonate, relative to sodium bicarbonate, with a small amount of bicarbonate decomposition to carbonate via loss of $CO_2$ during the experiment.

Example VII

This Example VII is presented to compare the solubilities of potassium carbonate and sodium carbonate in either monoethylene glycol (MEG) or diethylene glycol (DEG).

The solubilities of sodium carbonate and potassium carbonate in both MEG and DEG were examined at 90° C. by heating excess solid with either MEG or DEG in a block heater, with periodic shaking, followed by titration of a sample of supernatant with 0.1 NACl. Table 6 presents the results of the solubility measurements.

TABLE 6

Carbonate Solubility at 90° C.

| Cation | Solvent | Solubility equiv/Liter | Solubility $CO_3$ wt % |
|---|---|---|---|
| Na | MEG | 0.42 | 2.51 |
| K | MEG | 1.86 | 11.18 |
| Na | DEG | 0.07 | 0.43 |
| K | DEG | 1.60 | 9.61 |

The results presented in Table 6 show that the potassium carbonate has a substantially higher solubility in either MEG or DEG than does sodium carbonate.

Example VIII

This Example VIII is provided to demonstrate the effectiveness of certain soluble catalysts in catalyzing the hydrolysis of ethylene oxide (EO) to monoethylene glycol (MEG).

An independent series of experiments were conducted with a 550 ml autoclave filled with bicarbonate catalyst (0.1 mol of $HCO_3^-$), water (100 g; 5.55 mol) and EO (44 g; 1 mol) and heated over 15 min to 60° C. at 1500 kPa gas pressure. The reaction mixture was maintained under continuous stirring for 6-7 hours at the reaction temperature. At various time intervals, samples were taken for analysis. To study higher conversions some reactions were performed at higher temperatures.

The following homogeneous bicarbonate salts were evaluated: Sodium bicarbonate ($NaHCO_3$); Choline bicarbonate ($HO-CH_2-CH_2-N^+(CH_3)_3 \cdot HCO_3^-$); and Tetramethyl ammonium hydroxide (TMAH)($(CH_3)_4-N^+ \cdot OH^-$), under $CO_2$ the $OH^-$ is converted into bicarbonate ($HCO_3^-$).

To conduct a proper comparison, several of the experiments were performed under $CO_2$ pressure; since, carbon dioxide was needed to convert the TMAH catalyst into its bicarbonate form. An additional experiment was carried out with choline bicarbonate under nitrogen, to study possible differences.

The experimental results in terms of EO conversion and selectivity to MEG at approximately 2, 4 and 5 hours are compiled in Table 7. For comparison, the results of an uncatalyzed conversion of EO to glycols are also included. In addition, a measure for the catalyst activity is given, as reported for Table 1.

TABLE 7

Batch EO Hydrations to MEG Catalyzed by Homogeneous Bicarbonate Salts

| # | Catalyst | Gas Phase | Temp (° C.) | Time hr | % EO Converted | % MEG Selectivity | Overall rate 1/hr | Catalyst rate 1/hr(eq/L) |
|---|---|---|---|---|---|---|---|---|
| 4A | none-thermal | $N_2$ | 60 | 5 | 19.3 | 9.4 | 0.04 | na |
| 4B | none-thermal | $N_2$ | 120 | 2 | 49.4 | 81.0 | 1.73 | na |
| | | | | 4 | 99.9 | 67.6 | | |
| 4C | $NaHCO_3$ | $CO_2$ | 60 | 2 | 45.5 | 97.2 | 0.26 | 0.33 |
| | | | | 4 | 63.7 | 95.2 | | |
| | | | | 5 | 68.8 | 94.0 | | |
| 4D | choline bicarbonate | $CO_2$ | 60 | 2 | 32.8 | 98.0 | 0.17 | 0.19 |
| | | | | 4 | 47.9 | 97.3 | | |
| | | | | 5 | 50.0 | 98.2 | | |

TABLE 7-continued

Batch EO Hydrations to MEG Catalyzed by Homogeneous Bicarbonate Salts

| # | Catalyst | Gas Phase | Temp (° C.) | Time hr | % EO Converted | % MEG Selectivity | Overall rate 1/hr | Catalyst rate 1/hr(eq/L) |
|---|---|---|---|---|---|---|---|---|
| 4E | choline bicarbonate | $N_2$ | 60 | 2 | 47.1 | 97.9 | 0.26 | 0.33 |
| | | | | 4 | 61.0 | 96.8 | | |
| | | | | 5 | 68.3 | 95.7 | | |
| 4F | choline bicarbonate | $CO_2$ | 100 | 2 | 93.2 | 88.3 | 0.90 | 1.28 |
| | | | | 4 | 94.8 | 88.0 | | |
| | | | | 5 | 95.1 | 87.1 | | |
| 4G | TMAH | $CO_2$ | 60 | 2 | 22.8 | 98.1 | 0.15 | 0.16 |
| | | | | 4 | 47.5 | 97.1 | | |
| | | | | 5 | 54.7 | 96.4 | | |

The data presented in Table 7 show that the performance in terms of MEG selectivity at similar EO conversion for all the homogeneous catalysts is virtually identical (>95% at >50% conversion of EO) and significantly better than for the uncatalyzed thermal reaction. Also shown is that the performance in terms of catalytic activity (based on EO conversion) shows some variation for the homogeneous bicarbonate salts tested. The EO conversions for all catalyzed reactions are significantly higher than for the uncatalyzed thermal reaction.

Post reaction isolation of MEG product from the reaction mixture was briefly studied by flashing off the excess water. The sodium bicarbonate catalyst was observed to become insoluble in the remaining bottoms phase. In contrast, evaporation of the water of the reaction mixture originating from a choline bicarbonate catalyzed reaction resulted in a homogeneous catalyst/glycol mixture. This mixture can in principle be further purified by MEG distillation with recycle of catalyst at increased solubility.

While this invention has been described in terms of the presently preferred embodiment, reasonable variations and modifications are possible by those skilled in the art. Such variations and modifications are within the scope of the described invention and the appended claims.

The invention claimed is:

1. A process for manufacturing alkylene glycol, the process comprising:

subjecting a reaction mixture to suitable reaction conditions to thereby form a reaction product, wherein the reaction mixture comprises alkylene oxide, water and a soluble catalyst consisting essentially of a bicarbonate salt wherein the soluble catalyst has a solubility in monoethylene glycol exceeding about 5 weight percent at 25° C. and are sufficiently soluble in the product and the feed and any byproducts that said salts may be recycled without precipitating out of the recycle stream, and wherein the reaction product comprises alkylene glycol, water, the soluble catalyst and at least one reaction by-product;

separating the reaction product by distillation into an alkylene glycol product stream and a first recycle stream, wherein the alkylene glycol product stream comprises alkylene glycol, and wherein the first recycle stream comprises the soluble catalyst, decomposed soluble catalyst, and the at least one reaction by-product wherein the catalyst does not precipitate out of said first recycle stream;

contacting the first recycle stream with a gas comprising carbon dioxide under suitable conversion conditions to convert at least a portion of the decomposed soluble catalyst in the first recycle stream to the soluble catalyst; and subsequently combining the first recycle stream with the reaction mixture.

2. A process as recited in claim 1, further comprising:

separating the reaction product by distillation into a second recycle stream comprising water.

3. A process as recited in claim 2, further comprising:

combining the second recycle stream with the reaction mixture.

4. A process as recited in claim 1, further comprising:

yielding a purge stream comprising at least a portion of the first recycle stream.

5. A process as recited in claim 1 wherein the bicarbonate salt is selected from the group consisting of potassium bicarbonate, phosphonium bicarbonate, ammonium bicarbonate and choline bicarbonate.

6. A process as recited in claim 1 wherein the soluble catalyst has a solubility in monoethylene glycol exceeding about 6 weight percent.

7. A process for manufacturing alkylene glycol, wherein the process comprises the steps of:

introducing a reaction mixture into a reaction zone operated under suitable reaction conditions to thereby form a reaction product, wherein the reaction mixture comprises alkylene oxide, water and a soluble catalyst consisting essentially of a bicarbonate salt wherein the soluble catalyst has a solubility in monoethylene glycol exceeding about 5 weight percent at 25° C. and are sufficiently soluble in the product and the feed and any byproducts that said salts may be recycled without precipitating out of the recycle stream, and wherein the reaction product comprises alkylene glycol, water, the soluble catalyst and a reaction by-product;

withdrawing the reaction product as a withdrawn reaction product from the reaction zone;

introducing the withdrawn reaction product into a distillation system for separating the withdrawn reaction product into a product stream and a first recycle stream, wherein the product stream comprises alkylene glycol, and wherein the first recycle stream comprises the soluble catalyst, decomposed soluble catalyst, and the reaction by-product wherein the catalyst does not precipitate out of said first recycle stream;

contacting the first recycle stream with a gas comprising carbon dioxide under suitable conversion conditions to convert at least a portion of the decomposed soluble catalyst in the first recycle stream to the soluble catalyst; and subsequently adding the first recycle stream to the reaction mixture.

8. A process as recited in claim 7, wherein the bicarbonate salt is selected from the group consisting of potassium bicarbonate, phosphonium bicarbonate, ammonium bicarbonate and choline bicarbonate.

9. A process as recited in claim 7 wherein the distillation system further provides for separating the withdrawn reaction product into a second recycle stream comprising water.

10. A process as recited in claim 9, further comprising: adding the second recycle stream to the reaction mixture.

11. A process as recited in claim 7, further comprising: yielding from the distillation system a purge stream.

12. A process as recited in claim 1, wherein the soluble catalyst consists essentially of potassium bicarbonate.

13. A process as recited in claim 1, wherein the soluble catalyst consists essentially of ammonium bicarbonate.

* * * * *